United States Patent [19]

Hasegawa et al.

[11] Patent Number: 4,997,756
[45] Date of Patent: Mar. 5, 1991

[54] PROCESS FOR PREPARING SORBIC ACID

[75] Inventors: Masayasu Hasegawa, Kyoto; Yoh Honda, Hirakata, both of Japan

[73] Assignee: Nippon Gohsei Kagaku Kogyo Kabushiki Kaisha, Osaka, Japan

[21] Appl. No.: 405,924

[22] Filed: Sep. 12, 1989

[30] Foreign Application Priority Data

Sep. 14, 1988 [JP] Japan .................. 63-230534

[51] Int. Cl.$^5$ .......................... C12P 7/40; C12P 7/58; C12R 1/01; C12R 1/05
[52] U.S. Cl. ................................... 435/136; 435/137; 435/822; 435/823; 435/829; 435/886
[58] Field of Search ............... 435/136, 137, 822, 823, 435/829, 886

[56] References Cited

FOREIGN PATENT DOCUMENTS 63-152990 6/1988 Japan .

OTHER PUBLICATIONS

Derwent Abs. 88-216880/31 (J63152990, Jun. 25, 1988), Idemitsu Kosan KK.

*Primary Examiner*—Herbert J. Lilling
*Attorney, Agent, or Firm*—Armstrong, Nikaido, Marmelstein, Kubovcik & Murray

[57] ABSTRACT

A process for preparing sorbic acid which comprises treating sorbic aldehyde with at least one microorganism selected from Mycobacterium, Rhodopseudomonas, Streptomyces, Acetobacter, Alcaligenes and Gluconobacter. According to the present invention, sorbic acid can be prepared in high yield by oxidizing sorbic aldehyde with the specific microorganism.

2 Claims, No Drawings

PROCESS FOR PREPARING SORBIC ACID

BACKGROUND OF THE INVENTION

The present invention relates to a process for preparing sorbic acid, and more particularly to a process for preparing sorbic acid by microbiologically oxidizing sorbic aldehyde.

Sorbic acid and its salts have been preferably used as preservatives for foods because of their excellent antifungal activity. Sorbic acid has been industrially prepared by, ususally, reacting crotonaldehyde with a ketene to give a polyester through α-lactone produced as an intermediate, and decomposing the polyester with heat or an acid, or by using an ion exchange resin.

However, the above-mentioned process is not always advantageous in preparation and economy, that is, the recovering or purifying operation of sorbic acid after decomposing the polyester is troublesome, many steps and the complicated process control are required.

Recently, for solving the above disadvantages, Japanese Unexamined Patent Publication No. 152990/1988 has proposed a method wherein sorbic aldehyde is treated with a specific microorganism such as Pseudomonas to prepare sorbic acid. However, when conducting the method in an industrial scale, still it has been disadvantegeous in yield.

An object of the present invention is to provide a process for preparing sorbic acid in high yield.

This and other objects of the present invention will become apparent from the description hereinafter.

SUMMARY OF THE INVENTION

It has earnestly studied that sorbic acid is prepared according to microbiological treatment.

In accordance with the present invention, there is provided a process for preparing sorbic acid which comprises treating sorbic aldehyde with at least one microorganism selected from the group consisting of *Mycobacterium, Rhodopseudomonas, Streptomyces, Acetobacter, Alcaligenes* and *Gluconobacters*.

DETAILED DESCRIPTION

In the present invention, sorbic acid (2,4hexadienoic acid) is prepared by microbiologically oxidizing sorbic aldehyde (2,4-hexadienal).

The microorganism used in the present invention is at least one microorganism selected from the groups consisting of *Mycobacterium, Rhodopseudomonas, Streptomyces, Acetobacter, Alcaligenes* and *Gluconobacter*.

Concrete example of the microorganisms are, for instance, *Mycobacterium rhodochrous (Mycobacterium rhodochrous* IFO 13161), *Rhodopseudomonas spheroides (Rhodopseudomonas spheroides* IFO 12203), *Streptomyces albidoflavus (Streptomyces albidoflavus* IFO 13010), *Acetobacter ascendens (Acetobacter ascendens* IFO 3188), *Acetobacter pasteurianus subsp lovanien (Acetobacter pasteurianus subsp lovanien,* IFO 13753), *Alcaligenes eutrophus (Alcaligenes eutrophus* ATCC 17699), *Gluconobacter dioxyacetonics (Gluconobacter dioxyacetonics* IFO 3271), *Gluconobater gluconicus (Gluconobacter gluconicus* IFO 3171), *Gluconobacter oxydance (Gluconobacter oxydance* IFO 3189), *Gluconobacter rubiginosus (Gluconobacter rubiginosus* IFO 3244), *Gluconobacter suboxydans (Gluconobacter suboxydans* IFO 3254, *Gluconobacter suboxydans IFO* 3256), and the like. The term "IFO" and "ATCC" indicate the depositories "Institute for Fermentation, Osaka" and "American Type Culture Collection", respectively.

In the invention, any media can be used for culturing the microorganisms as mentioned above, so long as the medium contains a carbon source and a nitrogen source and the microorganisms can grow in the medium.

As the carbon source, any compounds can be used so long as the compound does not inhibit the activity of the microorganism for producing sorbic acid. Examples of the compounds used as the carbon source are, for instance, glucose, sucrose, ethanol, ethylene glycol, propylene glycol, 1,4-butanediol, glycerol, acetaldehyde, acetic acid, propionic acid, and the like.

As the nitrogen source there can be used, for instance, meat extract, peptone, corn steep liquor, urea, ammonium sulfate, ammonium chloride, sodium nitrate, and the like.

As occasion demands, inorganic salts such as phosphate, a magnesium salt, a calcium salt, an iron salt, a copper salt and a zinc salt, or nutrient substances necessary for growing the microorganisms can be suitably added to the medium.

When sorbic aldehyde is treated with the microorganisms, a culture broth containing the grown microorganism in the medium can be used as it is, and also a suspension wherein the microorganism collected from the broth is suspended in water, physiological siline or a buffer solution can be used.

The concentration of sorbic aldehyde in the reaction system is from about 0.01 to about 10 % by weight, preferably from about 0.05 to about 5 % by weight.

Sorbic aldehyde can be added to the broth or the suspension in any way, for instance, at once, separately or continuously. Practically, it is advantageous to add sorbic aldehyde intermittently. The microorganism is used in an amount of about 0.5 to about 20 g (as a dry weight of the microorganism) per $\epsilon$ of the suspension.

During the reaction of sorbic aldehyde with the microorganism, the reaction system is stirred under aerobic condition. For obtaining the aerobic condition, air or oxygen, and if necessary other gases, is blown into the reaction system. It is preferable that the oxygen content in the suspension is not less than 1 ppm.

It is preferable that the reaction is carried out at a temperature of 10° to 70° C., more preferably from 20° to 40° C. for about 0.1 to about 150 hours. Also, it is preferable that a pH of the system is from 4 to 9.

Also, a coenzyme such as PQQ (pyrroloquinoline quinone) or NAD(P) (nicotinamide adenine dinucleotide or its phosphate), a surfactant or an organic solvent may be suitably added to the reaction system.

In the present invention, the reaction can be conducted in any manner. For example, the reaction can be conducted, using either microorganisms which are growing or those which are resting or the both. Further, other immobilized microorganisms or extractives from the microorganisms may be used.

After the reaction is completed, the reaction mixture is purified in a usual manner to give the desired sorbic acid.

According to the present invention, sorbic acid can be prepared in high yield and high purify by oxidizing sorbic aldehyde with the specific microorganisms.

The present invention is more specifically described and explained by means of the following Examples. However, it is to be understood that the present invention is not limited to the Examples, and may be made various changes and modifications without departing from the scope or spirit of the present invention.

EXAMPLE 1

There were mixed 3 g of a meat extract, 10 g of pepton, 5 g of sodium chloride and 1 z of water to give a nutrient medium having a pH of 7. A test tube was charged with 5 ml of the nutrient medium, into which *Mycobacterium rhodochrous* IFO 13161 was inoculated in an amount of one platinum loop, and then cultured at 30° C. for 24 hours with shaking to give a seed culture broth.

A 500 ml Sakaguchi flask was charged with 100 ml of the nutrient medium, into which 5 ml of the seed culture broth was inoculated, and then was cultured with shaking at 30° C. for 24 hours. After culturing, cells were collected by centrifuging and washed with 0.1 M phosphate buffer (pH 7) to give 200 mg (dry weight) of cells.

A 400 ml L-shaped tube was charged with 60 mg (dry weight) of the cells, to which 10 ml of 0.01 M phosphate buffer was added and the cells was suspended thoroughly in the buffer. Then, 10 mg of sorbic aldehyde was added to the suspension to start the reaction.

The reaction was carried out with shaking at 30° C. for 30 minutes. After completing the reaction, the supernatant liquid was removed from the reaction mixture by centrifuging and adjusted to pH 2 with hydrochloric acid. A yield of the obtained sorbic acid was measured according to gas chromatopraphy.

The results are shown in Table 1.

The conditions in gas chromatography are as follows:
Apparatus: HEWLETT PACKARD 5890
Column: Quadrex Bonded, Fused Silica Capillary column
Methyl Sillicone 0.53 mm ×15 m ×8.0 µFilm
Column temperature: maintained at 80° C. for 8 minutes, elevated to 210° C. at rate of 15° C./minute, and maintained at 210° C. for 4 minute
Helium flow rate: 20 ml /minute
Detection: FID (Flame ionizaton detector)

EXAMPLES 2 TO 17

The procedure of Example 1 was repeated except that each microorganism shown in Table 1 was used.

The obtained sorbic acid was analyzed by gas chromatograph in the same manner as in Example 1.

The results are shown in Table 1.

TABLE 1

| Ex. | Microorganism | Yield of sorbic acid (%) |
|---|---|---|
| 1 | *Mycobacterium rhodochrous* IFO 13161 | 74 |
| 2 | *Phodopseudomonas spheroides* IFO 12203 | 73 |
| 3 | *Streptomyces albidoflavus* IFO 13010 | 69 |
| 4 | *Acetobacter ascendens* IFO 3188 | 70 |
| 5 | *Acetobacter pasteurianus subsp lovanien* IFO 13753 | 75 |
| 6 | *Alcaligenes eutrophus* ATCC 17699 | 70 |
| 7 | *Acetobacter acetigenus* IFO 3277 | 65 |
| 8 | *Acetobacer acetosus* IFO 3129 | 67 |
| 9 | *Acetobacter liquefaciens* IFO 12257 | 64 |
| 10 | *Acetobacter pasteurianus subsp estunens* IFO 13751 | 72 |
| 11 | *Acetobacter peroxydans* IFO 13755 | 63 |
| 12 | *Gluconobacter gluconicus* IFO 3171 | 58 |
| 13 | *Gluconobacter oxydance* IFO 3189 | 73 |
| 14 | *Gluconobacter rubiginosus* IFO 3244 | 49 |
| 15 | *Gluconobacter suboxydans* IFO 3254 | 72 |
| 16 | *Gluconobacter suboxydans* IFO 3256 | 71 |
| 17 | *Gluconobacter dioxyacetonics* IFO 3271 | 67 |

In addition to the ingredients used in the Examples, other ingredients can be used in Examples as set forth in the specification to obtain substantially the same results.

We claimed:

1. A process for preparing sorbic acid in a yield of at least 65% which comprises treating sorbic aldehyde with at least one microorganism selected from the group consisting of *Mycobacterium, Rhodopseudomonas, Streptomyces, Acetobacter, Alcaligenes, Gluconobacter oxydance, Gluconobacter suboxydans* and *Gluconobacter dioxyacetonics.*

2. A process according to claim 1, wherein said microorganism is at least one microorganism selected from the group consisting of *Micobacterium rhodochrous, Rhodopseudomonas spheroides, Streptomyces albidoflavus Acetobacter ascendens, Acetobacter pasteurianus subsp. lovanien, Acetobacter acetigenus, Acetobacter acetosus, Acetobacter liquefaciens, Acetobacter peroxydans, Alcaligenes eutrophus, Gluconobacter dioxyacetonics, Gluconobacter gluconicus, Gluconobacter oxydance, Gluconobacter suboxydans* and *Gluconobacter suboxydans.*

* * * * *